United States Patent [19]

Shinoda

[11] Patent Number: 5,393,919
[45] Date of Patent: Feb. 28, 1995

[54] PROCESS FOR PRODUCING ACETIC ACID OR METHYL ACETATE AND CATALYST THEREFOR

[75] Inventor: Sumio Shinoda, Tokyo, Japan

[73] Assignee: Daicel Chemical Industries, Ltd., Osaka, Japan

[21] Appl. No.: 204,343

[22] PCT Filed: Sep. 9, 1993

[86] PCT No.: PCT/JP93/01283
§ 371 Date: Mar. 9, 1994
§ 102(e) Date: Mar. 9, 1994

[87] PCT Pub. No.: WO94/05421
PCT Pub. Date: Mar. 17, 1994

[30] Foreign Application Priority Data

Sep. 10, 1992 [JP] Japan ................................. 4-269736

[51] Int. Cl.⁶ ...................... C07C 53/08; C07C 51/16; B01J 31/16; B01J 20/26
[52] U.S. Cl. ................................ 560/239; 502/313; 502/326; 502/402; 502/406
[58] Field of Search ................ 560/239; 502/402, 406, 502/313, 326

[56] References Cited

U.S. PATENT DOCUMENTS

| | | | |
|---|---|---|---|
| 4,061,558 | 12/1977 | Saito et al. | 204/290 F |
| 4,537,674 | 8/1985 | Ovshinsky et al. | 204/290 R |
| 4,626,334 | 12/1986 | Ohe et al. | 204/290 R |
| 5,214,184 | 5/1993 | Matuzaki et al. | 558/270 |

*Primary Examiner*—Arthur C. Prescott
*Attorney, Agent, or Firm*—Flynn, Thiel, Boutell & Tanis

[57] ABSTRACT

The present invention relates to:
(1) a novel catalyst which has a high catalytic activity, is useful in the production of acetic acid and/or methyl acetate from methanol, and is obtained through ion exchange of an anion of an anion exchanger with an anion of an Ru—Sn heteropolynuclear compound;
(2) a process for producing acetic acid and/or methyl acetate from methanol through a one-stage reaction in a gas phase wherein the catalytic activity is maintained throughout the reaction; and
(3) a process for producing acetic acid and/or methyl acetate in the presence of a highly active catalyst, for example, the catalyst specified in (1), at a high reaction rate.

21 Claims, No Drawings

PROCESS FOR PRODUCING ACETIC ACID OR METHYL ACETATE AND CATALYST THEREFOR

FIELD OF THE INVENTION

The present invention relates to a catalyst which is useful in the production of acetic acid and/or methyl acetate from methanol, and a process for producing acetic acid and/or methyl acetate by using methanol as a starting material through a one-stage reaction in a gas phase.

RELATED ART

Acetic acid has been industrially produced in a large amount by the methanol carbonylation method, i.e., so-called Monsanto's method. In this method, methanol is reacted with carbon monoxide in a liquid phase in the presence of a catalytic system containing a rhodium catalyst and an iodide.

However, it is necessary in these methods to use rhodium, which is highly expensive. Further, the conditions of location of the factory are restricted because it is necessary to obtain carbon monoxide of a high purity. Furthermore, there is a problem that methyl iodide, which is used as an iodide, corrodes the apparatus. In addition, since the above-mentioned reaction is usually effected in a liquid phase system containing water, the recovery of the acetic acid thus formed requires a lot of energy.

Meanwhile, there has been proposed the use of a Ru—Sn heteronuclear cluster (a polynuclear compound) containing an anion comprising $[Ru(SnCl_3)_5L]^{3-}$ (wherein L represents a ligand) as a catalyst for producing acetic acid and methyl acetate from methanol through a one-stage reaction in a liquid phase by Sumio Shinoda and Tetsu Yamakawa, "One-step Formation of Methyl Acetate with Methanol used as the Sole Source and Catalysis by $Ru^{II}$—$Sn^{II}$ Cluster Complexes", J. Chem. Soc., Chem. Commun., p.p. 1511–1512 (1990).

However, the above-mentioned heteronuclear cluster has a solubility in methanol as small as about 0.05 mM. In addition, since the above heteronuclear cluster is an anionic complex, the solubility of the above heteronuclear cluster is smaller not only in the acetic acid formed but also in common organic solvents. Thus, it is impossible to elevate the concentration of the catalyst, and therefore, the reaction rate also can not be enhanced. Furthermore, it is sometimes observed that formaldehyde is formed by the dehydrogenation of methanol and the metal contained in the catalyst is reduced and precipitated by the formaldehyde, which causes the deactivation of the catalyst within a short period of time. In particular, the catalyst is liable to be deactivated when reacted at a high temperature.

Accordingly, it is an object of the present invention to provide a novel catalyst which has a high catalytic activity and is useful for producing acetic acid and/or methyl acetate from methanol.

It is another object of the present invention to provide a process for producing acetic acid and/or methyl acetate from methanol through a one-stage reaction in a gas phase wherein the catalytic activity can be maintained at a high level throughout the reaction time.

It is another object of the present invention to provide a process for producing acetic acid and/or methyl acetate in the presence of a highly active catalyst at a high reaction rate.

DISCLOSURE OF THE INVENTION

The present inventor has extensively studied for achieving the above-mentioned objects. As a result, he has found that these objects can be achieved by reacting methanol in a gas phase with the use of a solid catalyst and that a specific catalyst with the use of an anion exchanger exhibits a high catalytic activity in a gas phase reaction where methanol is used as a starting material. The present inventor has further found that methylal or methyl formate can be produced by a gas phase reaction wherein methanol is used as a starting material and a solid catalyst is employed. Thus, the present invention has been completed based on these findings.

Thus, the present invention provides a catalyst prepared by exchanging an anion of an anion exchanger with an anion of an Ru—Sn hetero-polynuclear compound represented by the following general formula (1):

$$[Ru(SnX_3)_m(Y)_n]\cdot Z \qquad (1)$$

where X represents a halogen atom, an alkyl group, a cycloalkyl group, an aryl group, an aralkyl group or an alkoxyl group; Y represents a ligand; m is an integer of 1 to 6, n is an integer of 0 to 5 and m+n is an integer of 1 to 6; and Z represents a counter cation.

It is preferable that the above-mentioned Ru—Sn heteropolynuclear compound is represented by the general formula (1) wherein X is a halogen atom, Y is $PR^a_3$ or $R^bCN$ (wherein $R^a$ represents an alkyl group, a cycloalkyl group, an aryl group, an aralkyl group, an alkoxyl group, an aryloxy group or an arylalkoxyl group; and $R^b$ represents an alkyl group, a cycloalkyl group, an aryl group or an aralkyl group), m+n is 6 and n is 0 or 1.

The present invention further provides a process for producing acetic acid or methyl acetate characterized by dehydrogenating methanol in a gas phase in the presence of a solid catalyst.

Furthermore, the present invention provides a process for producing methylal or methyl formate characterized by using methanol as a starting material and effecting a gas phase reaction in the presence of a solid catalyst.

The scope and application of the present invention will become apparent from the following detailed description. However, it should be understood that the detailed description and examples, while indicating preferred embodiments of the invention, are given by way of illustration only, since various changes and modifications within the spirit and scope of the present invention will become apparent to those skilled in the art from this detailed description.

Though the present invention will be described in detail hereinafter, the scope of the present invention is not restricted by the following description.

The process according to the present invention is characterized in that acetic acid and/or methyl acetate or methylal and/or methyl formate are produced by a gas phase reaction by using methanol as a starting material.

The gas phase reaction is effected in the presence of a solid catalyst. As the solid catalyst, a heteronuclear cluster (a polynuclear compound) of Ru(II)—Sn(II) is preferable. In order to elevate the catalytic activity, it is particularly preferable to use a complex represented by the following general formula (1) as the Ru—Sn hetero-polynuclear compound.

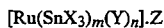

$$[Ru(SnX_3)_m(Y)_n] \cdot Z \qquad (1)$$

where X represents a halogen atom, an alkyl group, a cycloalkyl group, an aryl group, an aralkyl group or an alkoxyl group; Y represents a ligand; m is an integer of 1 to 6, n is an integer of 0 to 5 and m+n is an integer of 1 to 6; and Z represents a counter cation.

As the Ru—Sn hetero-polynuclear compound, it is preferable to use, among them, a complex represented by the general formula (1) wherein X is a halogen atom, Y is $PR^a_3$ or $R^bCN$ (wherein $R^a$ represents an alkyl group, a cycloalkyl group, an aryl group, an aralkyl group, an alkoxyl group, an aryloxy group or an arylalkoxyl group; and $R^b$ represents an alkyl group, a cycloalkyl group, an aryl group or an aralkyl group), m+n is 6 and n is 0 or 1.

Examples of the halogen atom represented by X in the above general formula (1) include a fluorine atom, a chlorine atom, a bromine atom and an iodine atom. As a preferable halogen atom, a chlorine atom may be cited.

Alternately, X may represents an alkyl group, a cycloalkyl group, an aryl group, an aralkyl group or an alkoxyl group.

Examples of the ligand represented by Y in the above general formula (1) include a halogen atom, a hydrogen atom, a coordinative carbon-containing ligand, a coordinative nitrogen-containing ligand, a coordinative oxygen-containing ligand, a coordinative phosphorus-containing ligand, a coordinative sulfur-containing ligand and a coordinative arsenic-containing ligand.

Now the ligand will be described more definitely.

The halogen atom as the ligand is the same as that represented by X. As a preferable halogen atom, a chlorine atom may be cited.

Examples of the "coordinative carbon-containing ligand" as used in the present invention include alkyl groups, cycloalkyl groups, aryl groups, aralkyl groups, monovalent cyclic dienyl groups such as a cyclopentadienyl group and a cyclooctadienyl group which may be substituted, olefins which may be substituted and CO.

Examples of the "coordinative nitrogen-containing ligand" as used in the present invention include $NH_3$, amines (for example, amines such as methylamine, ethylamine, dimethylamine and diethylamine, diamines such as ethylenediamine, nitrogen-containing heterocyclic compounds such as imidazole, pyridine, pyrimidine, piperidine, piperazine, morpholine and phenanthroline and nitrogen-containing aromatic compounds such as aniline) and compounds represented by $R^bCN$ (wherein $R^b$ represents an alkyl group, a cycloalkyl group, an aryl group, an aralkyl group or an alkoxyl group). Among these ligands, $NH_3$ is preferable.

Examples of the "coordinative oxygen-containing ligand" as used in the present inveniton include $H_2O$, alcohols including aliphatic alcohols and aromatic alcohols, ethers including aliphatic ethers and aromatic ethers, a hydroxyl ion and alkoxide ions.

Examples of the "coordinative phosphorus-containing ligand" as used in the present invention include $PR^a_3$ or $O=PR^a_3$ (wherein $R^a$ represents an alkyl group, a cycloalkyl group, an aryl group, an aralkyl group, an alkoxyl group, an aryloxy group or an arylalkoxyl group) and bis(diphenylphosphino)alkanes such as 1,2-bis(diphenylphosphino)ethane (dppe), 1,3-bis(diphenylphosphino)propane (dppp) and 1,4-bis(diphenylphosphino)butane (dppb), i.e., bidentate phosphine ligands. Since the bis(diphenylphosphino)alkanes have bidentate coordination characteristics, L represents ½{bis(diphenylphosphino)alkane}.

Examples of the "coordinative sulfur-containing ligand" as used in the present invention include compounds represented by RSR and RSH (wherein R represents an alkyl group, a cycloalkyl group, an aryl group, an aralkyl group or an alkoxyl group).

Examples of the "coordinative arsenic-containing ligand" as used in the present invention include compounds represented by $AsR_3$ or $O=AsR_3$ (wherein R represents an alkyl group, a cycloalkyl group, an aryl group, an aralkyl group or an alkoxyl group) and bidentate arsine ligands such as 1,2-bis(diphenylarsino)ethane. Since the 1,2-bis(diphenylarsino)ethane has bidentate coordination characteristics, L represents ½(1,2-bis(diphenylarsino)ethane).

Examples of the alkyl groups given in the description of X and Y in the above general formula (1) include a methyl group, an ethyl group, a n-propyl group, an isopropyl group, a n-butyl group, an isobutyl group, a pentyl group and a hexyl group.

Examples of the cycloalkyl groups include a cyclopentyl group, a cyclohexyl group and a cyclooctyl group. The aryl groups include a phenyl group, a naphthyl group and the like. The aralkyl groups include a benzyl group, a phenethyl group, a benzhydryl group and the like.

Examples of the alkoxyl groups include alkoxyl groups corresponding to the above-mentioned alkyl groups, for example, a methoxy group, an ethoxy group, a n-propoxy group, an isopropoxy group, a n-butoxy group, an isobutoxy group, a pentyloxy group and a hexyloxy group.

In the description of Y in the above general formula (1), examples of the aryloxy groups include a phenoxy group and a naphthoxy group, while examples of the arylalkoxyl groups include a phenylmethoxy group, a phenylethoxy and a phenylpropoxy group.

Examples of the counter cation represented by Z in the above-mentioned general formula (1) include a proton; alkali metal ions such as a lithium ion, a potassium ion and a sodium ion; alkaline earth metal ions such as a calcium ion and a barium ion; and cations represented by the general formula $XaH_4^+$, $XaH_3R^+$, $XaH_2R_2^+$, $XaHR_3^+$ or $XaR_4^+$ (wherein Xa represents N, P or As and R represents an alkyl group, a hydroxyalkyl group or an aryl group).

Examples of the alkyl group R in the above general formula representing the counter cation include linear and branched alkyl groups carrying about 1 to 4 carbon atoms such as a methyl group, an ethyl group and a propyl group. Examples of the hydroxyalkyl group include lower hydroxy alkyl groups carrying about 1 to 4 carbon atoms such as a hydroxymethyl group, a 2-hydroxyethyl group, a 2-hydroxypropyl group and a 3-hydroxypropyl group. Examples of the aryl group include a phenyl group.

As particular examples of the cation represented by the above-mentioned general formula, for example, quaternary ammonium ions such as an ammonium ion, a tetramethylammonium ion, a tetraethylammonium ion and a tetrapropylammonium ion; and quaternary phosphonium ions such as a phosphonium ion, a tetramethylphosphonium ion, a tetraethylphosphonium ion, a tetrahydroxymethylphosphonium ion and a tetraphenylphosphonium ion may be cited.

Among the complexes represented by the above general formula (1), the compounds represented by the general formula (1) wherein X is a halogen atom, Y is $PR^a_3$ or $R^bCN$ (wherein $R^a$ represents an alkyl group, a cycloalkyl group, an aryl group, an aralkyl group, an alkoxyl group, an aryloxy group or an arylalkoxyl group; and $R^b$ represents an alkyl group, a cycloalkyl group, an aryl group or an aralkyl group), m+n is 6 and n is 0 or 1 are preferable.

More particularly, the complexes represented by the above general formula (1) include those represented by the following general formulae (1a), (1b) and (1c):

  (1a)

  (1b)

  (1c)

wherein X represents a halogen atom, an alkyl group, a cycloalkyl group, an aryl group, an aralkyl group or an alkoxyl group; $R^a$ represents an alkyl group, a cycloalkyl group, an aryl group, an aralkyl group, an alkoxyl group, an aryloxy group or an arylalkoxyl group; $R^b$ represents an alkyl group, a cycloalkyl group, an aryl group or an aralkyl group; and Z represents a counter cation.

Preferable examples of the substituent $R^a$ in the compound represented by the general formula (1b) include aryl groups such as a phenyl group.

Preferable examples of the substituent $R^b$ in the compound represented by the general formula (1c) include alkyl groups carrying 1 to 3 carbon atoms, in particular, a methyl group.

The above-mentioned solid catalyst can be prepared by conventional techniques such as precipitation, impregnation and ion exchange.

The complex represented by the above general formula (1a) can be prepared, for example, in accordance with a method described in J. Chem. Soc., Dalton Trans., 2329 (1984). More particularly, it may be prepared by, for example, mixing a ruthenium halide, a tin halide and an acid such as hydrochloric acid, sulfuric acid and nitric acid, adding a solution of a compound corresponding to the counter cation Z thereto, collecting the precipitate thus formed and washing and drying the same. The completion of the reaction between the ruthenium halide and the tin halide can be judged depending on a change in the color of the solution.

The complex represented by the general formula (1c) can be prepared by mixing a complex represented by the formula $[RuX(SnX_3)_5].Z$ (wherein X and Z are as defined above) with a solution of a compound corresponding to $R^bCN$ (wherein $R^b$ is as defined above), adding, for example, $AgBF_4$ to the obtained reaction mixture, collecting the precipitate thus formed and washing and drying the same, see Can. J. Chem., 60, 1304 (1982).

Further, the complex represented by the general formula (1b) can be prepared by mixing a complex represented by the general formula (1c) with a solution of an organophosphorus compound corresponding to $PR^a_3$ (wherein $R^a_3$ is as defined above) at a temperature of, for example, around 50° to 80° C., collecting the precipitate thus formed and washing and drying the same. By this reaction, $R^bCN$ in the complex represented by the general formula (1c) is replaced by the organophosphorus compound to thereby give the complex represented by the general formula (1b).

The Ru—Sn hetero-polynuclear compound may be subjected to the reaction as a solid catalyst as such. However, it is preferable to use said compound in a state supported on a support so as to further elevate the catalytic activity.

Examples of the support include inorganic supports such as activated carbon, silica, alumina, silica-alumina, clay minerals, e.g., zeolite, copper oxide, bentonite, magnesia, silica-magnesia, titania and zirconia; and organic ones such as ion exchange resins and chelating resins. Among these supports, one comprising at least one member selected from the group consisting of inorganic supports such as activated carbon, silica, alumina, zeolite, copper oxide, titania and zirconia; and organic ones such as ion exchange resins and chelating resins are preferable. Preferable examples of the support include those which are resistant to high temperatures exceeding the reaction temperature.

The present invention is advantageous in that a support having a catalytic ability can be used. Examples of the support having a catalytic ability include those containing copper oxide. As the copper oxide, CuO and $Cu_2O$ may be cited. Divalent copper oxide, CuO, may be cited as a preferable copper oxide catalytic support.

The support having a catalytic ability may be a composite oxide system containing other metal oxide(s), in addition to the above copper oxide. Examples of the other oxides include various oxides, for example, oxides of elements of the group VIa in the periodic table (for example, $Cr_2O_3$, $CrO_3$ and $Mo_2O_3$) and oxides of elements of the group IIb in the periodic table (for example, ZnO and CdO). Examples of preferable composite oxides include those consisting of copper oxide and chromium oxide, e.g., $CuO—Cr_2O_3$ and $CuO—CrO_3$ and those consisting of copper oxide and zinc oxide, e.g., CuO—ZnO.

As additional preferable examples of the support, those wherein at least copper oxide, preferably the above-mentioned composite oxide, is supported on an inorganic support such as silica as cited above may be cited. When such a support is used, it is possible to extremely elevate (for example about 10- to 100-fold) the catalytic activity of the complex represented by the above genera formula (1), though the support per se has little catalytic activity.

A support containing copper oxide can be prepared in accordance with, for example, methods described in Japanese Patent Publication-A Nos. 68716/1978 and 108916/1978. That is to say, it can be prepared by impregnating a support with a solution of, for example, copper sulfate, copper nitrate, copper carbonate or copper acetate, followed by drying or baking. A support containing a composite oxide can be prepared by mixing the above-mentioned copper salt solution with a solution of, for example, sulfate, nitrate, acetate or carbonate of other metal(s) such as chromium and zinc and impregnating a support therewith, followed by baking.

A complex can be supported on a support by depositing a solution of the complex represented by the general formula (1) on the support or impregnating the support with said solution, or kneading a solution of the complex represented by the general formula (1) with the support, and drying the obtained mixture.

The amount of the catalyst to be supported can be selected over a wide range, so long as the efficiency for producing acetic acid and methyl acetate is not lowered thereby. For example, from 0.1 to 200 parts by weight, preferably from 1 to 100 parts by weight and still preferably from 5 to 80 parts by weight, of the catalyst may be used based on 100 parts by weight of the support.

A solid catalyst may be in any of the forms including powder, granule, pellet, bar, ellipsoid and sphere.

The above-mentioned Ru—Sn hetero-polynuclear compound is an anion complex. Thus, the solid catalyst may be obtained through ion exchange between an anion of an anion exchanger and an anion of an Ru—Sn hetero-polynuclear compound, in particular, a complex represented by the above-mentioned general formula (1). A compound obtained through ion exchange between an anion of an anion exchanger and an anion of a complex represented by the above-mentioned general formula (1) can be represented by the following general formula (3):

$$[Ru(SnX_3)_m(Y)_n] \cdot I \quad (3)$$

wherein I represents an anion exchanger; and X, Y, m and n are as defined above.

Such compounds, in particular, those represented by the general formula (3) are advantageous in having a higher catalytic activity than a solid catalyst carried on the above-mentioned support.

As the anion exchanger, for example, inorganic anion exchangers such as zirconium hydroxide, water-containing titania, for example, a compound represented by the compositional formula $TiO_2 \cdot zH_2O$ (wherein z represents a number not less than 0), water-containing zirconia, for example, a compound represented by the compositional formula $ZrO_2 \cdot zH_2O$ (wherein z represents a number not less than 0) and layered ion-exchangeable compounds; and anion exchange resins may be cited. Preferable examples of the anion exchanger include inorganic ion exchangers, in particular, hydrotalcite and hydrocalumite which are two dimensional layered compounds having an intercalated anion capable of undergoing ion exchange.

A compound obtained through ion exchange with an inorganic anion exchanger is advantageous in having a long catalytic life, which is seemingly caused by the pairing of the anion of the Ru—Sn hetero-polynuclear compound with the inorganic counter cation. Particularly, the effect can be highly achieved when an inorganic layered compound is used as an anion exchanger.

The above-mentioned hydrotalcite involves a series of compounds represented by a compositional formula (2) consisting of a brucite layer $[(Ma^{2+})_{2x}(Mb^{3+})_2(OH^-)_{4x+4}]^{2+}$, which is a positively charged hydroxide layer, an intercalated anion $[A^{y-}]_{2/y}$, and intercalated water:

$$[(Ma^{2+})_{2x}(Mb^{3+})_2(OH^-)_{4x+4}]^{2+} \cdot [A^{y-}]_{2/y} \cdot zH_2O \quad (2)$$

wherein $Ma^{2+}$ represents a divalent metal ion; $Mb^{3+}$ represents a trivalent metal ion; $A^{y-}$ represents a y-valent anion; x and y are natural numbers; and z represents a number not less than 0.

Examples of the above-mentioned divalent metal ion $Ma^{2+}$ include a magnesium ion, a nickel ion and a zinc ion. Examples of the trivalent metal ion $Mb^{3+}$ include an aluminum ion, a chromium ion and an iron ion.

In the above compositional formula (2), x is usually an integer of from 2 to S and y is 1 or 2. Examples of the above-mentioned anion $A^{y-}$ include inorganic ions such as a carbonate ion, a sulfate ion and halogen ions, e.g., a chloride ion; and organic anions such as a terephthalate ion.

The ion exchange of an anion exchanger with the above-mentioned Ru—Sn hetero-polynuclear compound can be effected by conventional ion exchange techniques.

When hydrotalcite is used as an anion exchanger and subjected to ion exchange by using a complex represented by the general formula (1) as the above-mentioned hetero-polynuclear compound, a solid catalyst, wherein the intercalated anion $A^{y-}$ of hydrotalcite has been ion-exchanged with an anion represented by the formula $[Ru(SnX_3)_m(Y)_n]$ wherein X, Y, m and n are as defined above, can be obtained.

When methanol is contacted with such a solid catalyst in a gas phase, acetic acid and/or methyl acetate is formed by a one-stage reaction. It is conceivable that this reaction proceeds as follows:

$$2CH_3OH \rightarrow 2HCHO + 2H_2$$

$$2HCHO \rightarrow HCOOCH_3$$

$$HCOOCH_3 \rightarrow CH_3COOH$$

$$CH_3COOH + CH_3OH \rightarrow CH_3COOCH_3 + H_2O$$

As these reaction formulae clearly show, the acetic acid thus formed further reacts with the methanol employed as the starting material to thereby give methyl acetate. Therefore, the formation of methyl acetate can be suppressed and acetic acid can be formed at a high efficiency by lowering the ratio of the methanol in the reaction system.

Under some reaction conditions, methyl formate and methylal, which are useful as precursors of acetic acid and methyl acetate, are formed as by-products in a relatively large amount. Accordingly, the process of the present invention is usable also as a process for producing methyl formate and/or methylal by appropriately selecting the reaction conditions.

Dehydrogenation of methanol in a gas phase can be effected at a temperature of, for example, from 50° to 400° C., preferably from about 100° to 300° C. This reaction is preferably effected in an inert gas (for example nitrogen gas, helium gas or argon gas) atmosphere under atmospheric or elevated pressure. The reaction may be carried out by any of the batchwise or continuous processes.

When the reaction is to be carried out batchwise, the ratio of methanol to the complex may be appropriately selected within such a range as not to lower the efficiency of the formation of acetic acid and methyl acetate. The ratio of methanol per mol of the complex is, for example, from 0.1 to 10,000 mol, preferably from about 10 to 1,000 mol.

A preferable method for dehydrogenating methanol in a gas phase includes a process wherein gaseous methanol is continuously supplied to the solid catalyst. In such a continuous process, the feed rate of methanol per mol of the complex can be selected within such a wide range as not to lower the efficiency of the formation of acetic acid and methyl acetate, for example, from 0.001 to 1,000 mol/min, preferably from about 0.01 to 100 mol/min.

In the case of a continuous process, any of the conventional processes, for example, a flow-through reaction system wherein gaseous methanol is supplied to a bed packed with a solid catalyst, a reaction system wherein a solid catalyst is suspended in gaseous methanol to thereby form a fluidized bed, or a reaction distillation system is usable. Among the continuous methods, the flow-through reaction system is preferable.

The catalyst of the present invention has a high activity, and therefore, the catalyst is useful in the production of acetic acid and/or methyl acetate through a one-stage reaction starting with methanol. In particular, a solid catalyst prepared by using hydrotalcite has a high catalytic activity and a long catalytic life.

In the process of the present invention, methanol is dehydrogenated in a gas phase in the presence of a solid catalyst, which makes it possible to elevate the concentration of the catalyst. Therefore, the process of the present invention is advantageous in that the reaction rate can be enhanced. In addition, the process of the present invention is scarcely accompanied by the deposition of metals from the catalyst, which has become a problem in reactions for synthesizing acetic acid or methyl acetate from methanol in a homogeneous liquid phase catalyst system. Accordingly, the catalyst is hardly deactivated even though the reaction is effected at high temperature. In the process of the present invention, therefore, the catalytic activity can be maintained over a prolonged period of time.

In addition, when a solid catalyst comprising an Ru—Sn hetero-polynuclear compound supported on a support such as activated carbon is used in the process of the present invention, acetic acid and/or methyl acetate can be produced at a high efficiency based on the high catalytic activity of the catalyst.

When said Ru—Sn hetero-polynuclear compound is a complex represented by the above-mentioned general formula (1), the productivity of acetic acid and/or methyl acetate is further elevated on the basis of the further improved catalytic activity of said complex.

When a solid catalyst obtained through ion exchange between the anion of an anion exchanger such as hydrotalcite and the anion of an Ru—Sn hetero-polynuclear compound is used, acetic acid and/or methyl acetate can be efficiently produced on the basis of the further improved catalytic activity and the prolonged catalytic life of said solid catalyst.

EXAMPLES

Though the present invention will be described in greater detail with reference to the Examples hereinafter, it is to be understood that the scope of the present invention is not limited thereto.

In the following Examples and Comparative Examples, acetic acid and/or methyl acetate was synthesized by using a pulse reactor and each reaction product was determined by gas chromatography, except that in Example 6, acetic acid and/or methyl acetate were synthesized by a fixed bed flow-through system under atmospheric pressure.

PREPARATION 1 OF COMPLEX-SUPPORTING CATALYST (1) Preparation of $\{(Ph_3P)_2N\}_4[Ru(SnCl_3)_6]$ $\{(Ph_3P)_2N\}_4[Ru(SnCl_3)_6]$ (wherein Ph represents a phenyl group) was prepared in accordance with a method described in J. Chem. Soc., Dalton Trans., 2329 (1984).

(2) Preparation of Support 722.9 parts by weight of copper nitrate (trihydrate) was dissolved in 1,500 parts by weight of water to prepare a solution A. Separately, 1253.2 parts by weight of chromium nitrate (nonahydrate) was dissolved in 7,500 parts by weight of water to prepare a solution B.

The solutions A and B were mixed together. Then 5,000 parts by weight of silica, mfd. by Kanto Chemical Co., Ltd.; silicic anhydride, was impregnated with the mixed solution thus obtained and heated at 120° to 180° C. for 1 to 3 hours to thereby remove the water and to dry. The support thus obtained was baked at 650° C. for 8 hours. Thus $CuO-Cr_2O_8/SiO_2$ was obtained.

(3) Preparation of Complex-supporting Catalyst 0.901 g of the $\{(Ph_3P)_2N\}_4[Ru(SnCl_3)_6]$ prepared in (1) was dissolved in acetonitrile to prepare 50 ml of a solution. The solution thus obtained was used to impregnate 1.0 g of the $CuO-Cr_2O_3/SiO_2$ prepared in (2). After drying in a vacuum at 25° C. for 15 hours, a complex-supporting catalyst was prepared.

Example 1

0.1 g of the $\{(Ph_3P)_2N\}_4[Ru(SnCl_3)_6]/CuO-Cr_2O_3/SiO_2$, i.e., the complex-supporting catalyst prepared in "Preparation 1 of complex-supporting catalyst" (amount of the supported complex: $1.3 \times 10^{-5}$ mol) was packed in a reactor and treated by passing helium gas through the reactor at a temperature of 200° C. and at a flow rate of 25 ml/min for 3 hours.

Next, 1 μl ($2.47 \times 10^{-5}$ mol) of methanol was introduced into the reactor at a temperature of 200° C. by using helium gas as a carrier (flow rate: 25 ml/min). Thus, $0.004 \times 10^{-5}$ mol of acetic acid, $0.006 \times 10^{-5}$ mol of methyl acetate, $0.001 \times 10^{-5}$ mol of methyl formate and $0.001 \times 10^{-5}$ mol of methylal were formed.

PREPARATION 2 OF COMPLEX-SUPPORTING CATALYST (1) Preparation of $(NEt_4)_3[RuCl(SnCl_3)_5]$ $(NEt_4)_3[RuCl(SnCl_3)_5]$ (wherein Et represents an ethyl group) was prepared in accordance with a method described in J. Farrugia, et al., Can. J. Chem., 66, 1304 (1982).

(2) Preparation of $(NEt_4)_3[Ru(SnCl_3)_5(CH_3CN)]$ 1.1 g of the $(NEt_4)_3[RuCl(SnCl_3)_5]$ prepared in (1) was dissolved in acetonitrile to prepare 40 ml of a solution. To this solution was added 0.14 g of $AgBF_4$ and the precipitate thus formed was collected by filtration. The substance obtained by the filtration was washed with acetone and dried. Thus, 0.8 (yield: 77% on the basis of Ru) of yellow powdery crystals, i.e., $(NEt_4)_3[Ru(SnCl_3)_5(CH_3CN)]$ was obtained.

(3) Preparation of Complex-supporting Catalyst 0.833 g of the $(NEt_4)_3[Ru(SnCl_3)_5(CH_3CN)]$ prepared in (2) was dissolved in acetone to prepare 65 ml of a solution. The obtained solution was used to impregnate 1.58 g of activated carbon [mfd. by Kansai Coke and Chemicals Co., Ltd.; Maxsorb, BET specific surface area: 3,100 m²/g] and dried in a vacuum at 25° C. for 15 hours to thereby prepare a complex-supporting catalyst.

Example 2

0.1 g of the $(NEt_4)_3[Ru(SnCl_3)_5(CH_3CN)]$/activated carbon, i.e., the complex-supporting catalyst prepared in "Preparation 2 of the complex-supporting catalyst" (amount of the supported complex: $1.05 \times 10^{-5}$ mol) was packed in a reactor and treated by passing helium gas through the reactor at a temperature of 300° C. and at a flow rate of 25 ml/min for 3 hours.

Next, 1 μl (2.47×10$^{-5}$ mol) of methanol was introduced into the reactor at a temperature of 300° C. by using helium gas as a carrier (flow rate: 25 ml/min). Thus, 0.001×10$^{-5}$ mol of acetic acid, 0.002×10$^{-5}$ mol of methyl acetate, 0.043×10$^{-5}$ mol of methyl formate and 0.005×10$^{-5}$ mol of methylal were formed.

PREPARATION 3 OF COMPLEX-SUPPORTING CATALYST (1) Preparation of (NEt$_4$)$_4$[Ru(SnCl$_3$)$_6$]

(NEt$_4$)$_4$[Ru(SnCl$_3$)$_6$] (wherein Et represents an ethyl group) was prepared in accordance with a method described in J. Chem. Soc., Dalton Trans., 2329 (1984).

Namely, in an argon gas atmosphere, 10 ml of 2M hydrochloric acid was added to a mixture of 0.5 g (1.91 mmol) of RuCl$_3$.3H$_2$O and 4.8 g (19 mmol) of SnCl$_2$.2H$_2$O. The obtained mixture was stirred at 90° C. for 12 hours. During this period, the solution turned from dark brown into yellow finally. The reaction mixture was cooled to room temperature and then a solution of 1.26 g (7.6 mmol) of NEt$_4$Cl (wherein Et represents an ethyl group) in 10 ml of 2M hydrochloric acid was dropwise added thereto to thereby form a yellow precipitate. The yellow precipitate was collected by filtration, successively washed with 2M hydrochloric acid, ethanol and diethyl ether and dried in a vacuum. Thus, yellow powdery crystals were obtained (yield: 2.34 g, 62% on the basis of Ru).

(2) Preparation of Support 200 g of cupric acetate, 15 g of zinc carbonate and 10 g of silica, mfd. by Kanto Chemical Co., Ltd.; silicic anhydride, were kneaded together with 80 ml of water for 3 hours. The mixture thus obtained was dried in a nitrogen gas atmosphere at 80° C. for 8 hours and then baked in a nitrogen atmosphere at 650° C. for 3 hours to thereby give a support. The resulting support comprised 80% by weight of CuO, 10% by weight of ZnO and 10% by weight of SiO$_2$.

(3) Preparation of Complex-supporting Catalyst 0.0986 g of the (NEt$_4$)$_4$[Ru(SnCl$_3$)$_6$] prepared in (1) was dissolved in acetonitrile to prepare 10 ml of a solution. The solution thus obtained was used to impregnate 1.0 g of the support CuO—ZnO/SiO$_2$ prepared in (2). After drying in a vacuum at 25° C. for 15 hours, a complex-supporting catalyst was prepared.

Example 3

0.1 g of the (NEt$_4$)$_4$[Ru(SnCl$_3$)$_6$]/CuO—ZnO/SiO$_2$, i.e., the complex-supporting catalyst prepared in "Preparation 3 of complex-supporting catalyst" (amount of the supported complex: 4.61×10$^{-6}$ mol) was packed in a reactor and treated by passing helium gas through the reactor at a temperature of 200° C. and at a flow rate of 25 ml/min for 3 hours.

Next, 1 μl (2.47×10$^{-5}$ mol) of methanol was introduced into the reactor at a temperature of 200° C. by using helium gas as a carrier (flow rate: 25 ml/min). Thus, 0.0001×10$^{-5}$ mol of acetic acid, 0.003×10$^{-5}$ mol of methyl acetate and 0.02×10$^{-5}$ mol of methyl formate were formed.

PREPARATION 4 OF COMPLEX-SUPPORTING CATALYST 0.0829 g of the (NEt$_4$)$_3$[Ru(SnCl$_3$)$_5$(CH$_3$CN)] prepared in "Preparation 2-(2) of complex-supporting catalyst" was dissolved in acetone to prepare 20 ml of a solution. The obtained solution was used to impregnate 1.0 g of the support CuO—ZnO/SiO$_2$ prepared in "Preparation 3-(2) of complex-supporting catalyst" and dried in a vacuum at 25° C. for 15 hours to thereby prepare a complex-supporting catalyst.

Example 4

0.1 g of the (NEt$_4$)$_3$[Ru(SnCl$_3$)$_5$(CH$_3$CN)]/CuO—ZnO/SiO$_2$, i.e., the complex-supporting catalyst prepared in "Preparation 4 of complex-supporting catalyst" (amount of the supported complex: 4.64×10$^{-6}$ mol) was packed in a reactor and then treated in the same manner as described in Example 3. Next, 1 μl (2.47×10$^{-5}$ mol) of methanol was introduced into the reactor at a temperature of 200° C. by using helium gas as a carrier (flow rate: 25 ml/min). Thus, 0.0001×10$^{-5}$ mol of acetic acid, 0.0003×10$^{-5}$ mol of methyl acetate, 0.010×10$^{-5}$ mol of methyl formate and 0.0001×10$^{-5}$ mol of methylal were formed.

PREPARATION 5 OF COMPLEX-SUPPORTING CATALYST 0.800 g of the (NEt$_4$)$_4$[Ru(SnCl$_3$)$_6$] prepared in "Preparation 3-(1) of complex-supporting catalyst" was dissolved in acetonitrile to thereby obtain 20 ml of a solution. The solution was used to impregnate 1.00 g of activated carbon, mfd. by Kansai Coke and Chemicals Co., Ltd.; Maxsorb, BET specific surface area: 3,100 m$^2$/g, and dried in a vacuum at 25° C. for 15 hours to thereby prepare a complex-supporting catalyst.

Example 5

0.1 g of the (NEt$_4$)$_4$[Ru(SnCl$_3$)$_6$]/activated carbon, i.e., the complex-supporting catalyst prepared in the above "Preparation 5 of complex-supporting catalyst" (amount of the supported complex: 2.25×10$^{-5}$ mol) was packed in a reactor and treated by passing helium gas through the reactor at a temperature of 200° C. and at a flow rate of 25 ml/min for 3 hours.

Next, 1 μl (2.47×10$^{-5}$ mol) of methanol was introduced into the reactor at a temperature of 200° C. by using helium gas as a carrier (flow rate: 25 ml/min). Thus, 5.46×10$^{-9}$ mol of acetic acid, 1.39×10$^{-8}$ mol of methyl acetate, 1.19×10$^{-8}$ mol of methyl formate and 6.30×10$^{-8}$ mol of methylal were formed.

PREPARATION 6 OF COMPLEX-SUPPORTING CATALYST (1) Preparation of Hydrotalcite Having Intercalated Terephthalate Anion [Mg$_4$Al$_2$(OH)$_{12}$]$^{2+}$(C$_6$H$_4$(COO$^-$)$_2$).zH$_2$O Hydrotalcite having an intercalated terephthalate anion was prepared in accordance with a method described in Inorg. Chem., 27, 4628 (1988). All procedures were effected in an argon atmosphere.

Namely, 13.3 g of terephthalic acid and 57.5 g of a 50% by weight aqueous solution of sodium hydroxide were added to 160 ml of water and the obtained mixture was heated to 60° C. and then allowed to cool to room temperature.

Then, into the solution thus obtained was dropwise added 128 ml of an aqueous solution obtained by dissolving 41.0 g of Mg(NO$_3$)$_2$.6H$_2$O and 30.0 g of Al(NO$_3$)$_3$.9H$_2$O over 90 minutes under stirring. This solution was allowed to stand at 73° C. for 18 hours and the precipitate thus formed was collected by filtration and thoroughly washed with water.

The substance obtained by filtration was dried in a vacuum at 120° C. for 15 hours and ground in an agate mortar. Thus, the title compound was obtained in the form of a powder.

(2) Preparation of a Catalyst Having Ru—Sn Hetero-polynuclear Compound Supported on Hydrotalcite All of the following procedures were effected in an argon atmosphere.

1.00 g of $RuCl_3.3H_2O$ and 8.60 g of $SnCl_2.2H_2O$ were dissolved in 120 ml of 2N hydrochloric acid. The obtained mixture was heated at 90° C. for 12 hours. The obtained solution was passed through an anion exchange resin (Dowex 1X-8, 100-200 mesh) to thereby remove anions other than $[Ru(SnCl_3)_6]^{4-}$ therefrom.

To the solution thus obtained was added 4.00 g of $[Mg_4Al_2(OH)_{12}]^{2+}(C_6H_4(COO^-)_2).zH_2O$ prepared in (1). Ion exchange was effected by stirring the mixture at 40° C. for 12 hours. The solid matters were collected by filtration, washed with dilute hydrochloric acid and dried in a vacuum at 150° C. for 4 hours to thereby obtain a yellow powder.

The result of an analysis on the composition of the powder thus obtained by the ICP (inductively coupled plasma) spectrometry indicated Ru:Sn:Al:Mg=1:6.5:4.7:7.9. Based on this result, it is considered that the obtained powder roughly has a composition $[Mg_8Al_4(OH)_{24}]^{4+}[Ru(SnCl_3)_6]^{4-}.zH_2O$. Further, the result of XRD (x-ray diffractometry) indicated that the interlayer distance was 17 Å.

Example 6

0.3 g of the catalyst obtained in the above "Preparation 6 of complex-supporting catalyst" was packed in a reactor. A mixed gas comprising 10% by mol of methanol and 90% by mol of helium was continuously supplied to the reactor at a temperature of 200° C. and at a flow rate of 6.2 ml/min. 10 minutes after the initiation of the supply of the gas, the gas produced by the reaction was analyzed. As a result, it was found out that the yields of acetic acid, methyl formate and methylal were respectively 4.2%, 3.0% and 4.6%.

Comparative Example 1

The same experiment as that of Example 1 was conducted except that the complex-supporting catalyst employed in Example 1 was replaced by 0.1 g of the $CuO—Cr_2O_3/SiO_2$ which was the support employed in "Preparation 1 of complex-supporting catalyst". As a result, neither acetic acid nor methyl acetate but $0.019 \times 10^{-5}$ mol of methyl formate alone was detected as a reaction product.

Comparative Example 2

The same experiment as that of Comparative Example 1 was conducted except that 0.53 g of $CuO—Cr_2O_3/SiO_2$ was used. As a result, neither acetic acid nor methyl acetate but $0.011 \times 10^{-5}$ mol of methyl formate alone was detected as a reaction product.

Comparative Example 3

The same experiment as that of Example 1 was conducted except that the complex-supporting catalyst employed in Example 1 was replaced by 0.1 g of the $CuO—ZnO/SiO_2$ which was the support employed in "Preparation 3 of complex-supporting catalyst". As a result, neither acetic acid nor methyl acetate but $0.037 \times 10^{-5}$ mol of methyl formate alone was detected as a reaction product.

Comparative Example 4

The same experiment as that of Example 1 was conducted except that the complex-supporting catalyst employed in Example 1 was replaced by 0.1 g of the activated carbon, mfd. by Kansai Coke and Chemicals Co., Ltd.; Maxsorb, BET specific surface area: 3,100 $m^2/g$, which was the support employed in "Preparation 2 of complex-supporting catalyst". As a result, the methanol employed as the starting material was recovered at a ratio of 100%.

Comparative Example 5

The same experiment as that of Example 1 was conducted except that the complex-supporting catalyst employed in Example 1 was replaced by 0.1 g of the hydrotalcite having an intercalated terephthalate anion obtained in "Preparation 6-(1) of complex-supporting catalyst". As a result, no dehydrogenation product of methanol was detected as a reaction product.

I claim:

1. A catalyst obtained by ion exchanging an anion of an anion exchanger with an anion of an Ru—Sn hetero-polynuclear compound represented by the following general formula (1):

$$[Ru(SnX_3)_m(Y)_n].Z \qquad (1)$$

wherein X represents a halogen atom, an alkyl group, a cycloalkyl group, an aryl group, an aralkyl group or an alkoxyl group; Y represents a ligand; m is an integer of 1 to 6, n is an integer of 0 to 5 and m+n is an integer of 1 to 6; and Z represents a counter cation.

2. The catalyst as claimed in claim 1, wherein said Ru—Sn hetero-polynuclear compound is one represented by the general formula (1) wherein X is a halogen atom; Y is $PR^a_3$ or $R^bCN$, wherein $R^a$ represents an alkyl group, a cycloalkyl group, an aryl group, an aralkyl group, an alkoxyl group, an aryloxy group or an arylalkoxyl group; and $R^b$ represents an alkyl group, a cycloalkyl group, an aryl group or an aralkyl group), m+n is 6 and n is 0 or 1.

3. The catalyst as claimed in claim 1, wherein said Ru—Sn hetero-polynuclear compound is one represented by the general formula (1) wherein X is an alkyl group, a cycloalkyl group, an aryl group, an aralkyl group or an alkoxyl group.

4. The catalyst as claimed in claim 1 wherein said anion exchanger is hydrotalcite.

5. The catalyst as claimed in claim 4 wherein said hydrotalcite is one represented by the following compositional formula (2):

$$[(M^{a2+})_{2x}(M^{b3+})_2(OH)_{4x+4}]^{2+}.[A^{y-}]_{2/y}.zH_2O \qquad (2)$$

wherein $M^{a2+}$ represents a divalent metal ion; $M^{b3+}$ represents a trivalent metal ion; $A^{y-}$ represents a y-valent anion; x and y are natural numbers; and z represents a number not less than 0.

6. The catalyst as claimed in claim 1 wherein the anion exchanger is hydrocalumite.

7. The catalyst as claimed in claim 1 represented by the following general formula (3):

$$[Ru(SnX_3)_m(Y)_n].I \qquad (3)$$

wherein X represents a halogen atom, an alkyl group, a cycloalkyl group, an aryl group, an aralkyl group or an alkoxyl group; Y represents a ligand; m is an integer of 1 to 6, n is an integer of 0 to 5 and m+n is an integer of 1 to 6; and I represents a anion exchanger.

8. The catalyst as claimed in claim 7 represented by the general formula (3) wherein X is a halogen atom; Y is $PR^a{}_3$ or $R^bCN$, wherein $R^a$ represents an alkyl group, a cycloalkyl group, an aryl group, an aralkyl group, an alkoxyl group, an aryloxy group or an arylalkoxyl group; and $R^b$ represents an alkyl group, a cycloalkyl group, an aryl group or an aralkyl group, m+n is 6 and n is 0 or 1.

9. A process for producing acetic acid and/or methyl acetate characterized by effecting dehydrogenation of methanol in a gas phase in the presence of a solid catalyst.

10. The process for producing acetic acid and/or methyl acetate as claimed in claim 9, wherein the solid catalyst comprises an Ru—Sn hetero-polynuclear compound.

11. The process for producing acetic acid and/or methyl acetate as claimed in claim 9, wherein the solid catalyst comprises an Ru—Sn hetero-polynuclear compound supported on a support.

12. The process for producing acetic acid and/or methyl acetate as claimed in claim 11, wherein the support comprises at least one substance selected from the group consisting of activated carbon, silica, a clay mineral, copper oxide, alumina, titania and zirconia.

13. The process for producing acetic acid and/or methyl acetate as claimed in claim 9, wherein the solid catalyst is one obtained through ion exchange of an anion of an anion exchanger with an anion of an Ru—Sn hetero-polynuclear compound.

14. The process for producing acetic acid and/or methyl acetate as claimed in claim 18, wherein the Ru—Sn hetero-polynuclear compound is a complex represented by the following general formula (1):

$$[Ru(SnX_3)_m(Y)_n] \cdot Z \qquad (1)$$

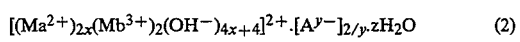

wherein X represents a halogen atom, an alkyl group, a cycloalkyl group, an aryl group, an aralkyl group or an alkoxyl group; Y represents a ligand; m is an integer of 1 to 8, n is an integer of 0 to 5 and m+n is an integer of 1 to 6; and Z represents a counter cation.

15. The process for producing acetic acid and/or methyl acetate as claimed in claim 14, wherein said Ru—Sn hetero-polynuclear compound is one represented by the general formula (1) wherein X is a halogen atom; Y is $PR^a{}_3$ or $R^bCN$, wherein $R^a$ represents an alkyl group, a cycloalkyl group, an aryl group, an aralkyl group, an alkoxyl group, an aryloxy group or an arylalkoxyl group; and $R^b$ represents an alkyl group, a cycloalkyl group, an aryl group or an aralkyl group, m+n is 6 and n is 0 or 1.

16. The process for producing acetic acid and/or methyl acetate as claimed in claim 14, wherein said Ru—Sn hetero-polynuclear compound is one represented by the general formula (1), wherein X is an alkyl group, a cycloalkyl group, an aryl group, an aralkyl group or an alkoxyl group.

17. The process for producing acetic acid and/or methyl acetate as claimed in claim 13 wherein the anion exchanger is hydrotalcite.

18. The process for producing acetic acid and/or methyl acetate as claimed in claim 17 wherein the hydrotalcite is one represented by the following compositional formula (2):

$$[(Ma^{2+})_{2x}(Mb^{3+})_2(OH^-)_{4x+4}]^{2+} \cdot [A^{y-}]_{2/y} \cdot zH_2O \qquad (2)$$

wherein $Ma^{2+}$ represents a divalent metal ion; $Mb^{3+}$ represents a trivalent metal ion; $A^{y-}$ represents a y-valent anion; x and y are natural numbers; and z represents a number not less than 0.

19. The process for producing acetic acid and/or methyl acetate as claimed in claim 13 wherein the anion exchanger is hydrocalumite.

20. The process for producing acetic acid and/or methyl acetate as claimed in claim 13 wherein the substance obtained through ion exchange of an anion of an anion exchanger with an anion of an Ru—Sn heteropolynuclear compound is one represented by the following general formula (3):

$$[Ru(SnX_3)_m(Y)_n] \cdot I \qquad (3)$$

wherein X represents a halogen atom, an alkyl group, a cycloalkyl group, an aryl group, an aralkyl group or an alkoxyl group; Y represents a ligand; m is an integer of 1 to 6 and n is an integer of 0 to 5, provided that m+n is an integer of 1 to 6; and I represents an anion exchanger.

21. The process for producing acetic acid and/or methyl acetate as claimed in claim 20 wherein the substance obtained through ion exchange of an anion of an anion exchanger with an anion of an Ru—Sn heteropolynuclear compound is one represented by the above general formula (3) wherein X is a halogen atom; Y is $PR^a{}_3$ or $R^bCN$, wherein $R^a$ represents an alkyl group, a cycloalkyl group, an aryl group, an aralkyl group, an alkoxyl group, an aryloxy group or an arylalkoxyl group; and $R^b$ represents an alkyl group, a cycloalkyl group, an aryl group or an aralkyl group, m+n is 6 and n is 0 or 1.

* * * * *

UNITED STATES PATENT AND TRADEMARK OFFICE
CERTIFICATE OF CORRECTION

PATENT NO. : 5 393 919
DATED : February 28, 1995
INVENTOR(S) : Sumio Shinoda

It is certified that error appears in the above-indentified patent and that said Letters Patent is hereby corrected as shown below:

Column 14, line 41;   change "group)," to ---group,---.
Column 14, line 54;   change "(OH)" to ---(OH$^-$)---.
Column 15, line 35;   change "18" to ---13---.

Column 16, line 29;   change "hereto-" to ---hetero- ---.

Signed and Sealed this

Eleventh Day of July, 1995

Attest:

BRUCE LEHMAN

Attesting Officer    Commissioner of Patents and Trademarks